(12) United States Patent
Mahalingam et al.

(10) Patent No.: US 6,551,581 B1
(45) Date of Patent: Apr. 22, 2003

(54) METHODS FOR IMPROVING THE AESTHETIC APPEARANCE OF SKIN AND HAIR

(75) Inventors: Harish Mahalingam, Ledgewood, NJ (US); Brian Jones, Warwick, NY (US); Christos D. Kyrou, Goshen, NY (US); Michael Traudt, Brookfield, CT (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/033,180

(22) Filed: Dec. 27, 2001

(51) Int. Cl.[7] .............................. A61K 7/42; A61K 7/44; A61K 7/00; A61K 7/06
(52) U.S. Cl. ........................ 424/59; 424/60; 424/70.1; 424/400; 424/401
(58) Field of Search ............................ 424/59, 60, 400, 424/401, 70.1

(56) References Cited

U.S. PATENT DOCUMENTS 5,998,423 A    12/1999    Manneth et al. ............ 514/260

*Primary Examiner*—Shelley A. Dodson
(74) *Attorney, Agent, or Firm*—Ohlandt, Greeley, Ruggiero & Perle, L.L.P.

(57) ABSTRACT

The present invention provides methods for increasing pigmentation in skin and/or hair. Also, the present invention provides self-tanning compositions and methods that increase pigmentation in skin and/or hair. The preferred methods and compositions of the present invention have methylthioadenosine.

20 Claims, 2 Drawing Sheets

(1 of 2 Drawing Sheet(s) Filed in Color)

72  48  24  12  Hours 0.02%

0.05%

None

METHODS FOR IMPROVING THE AESTHETIC APPEARANCE OF SKIN AND HAIR

BACKGROUND OF THE INVENTION

1. Field of the Invention

The present invention relates to methods of improving the aesthetic appearance of skin and/or hair. More particularly, the present invention relates to methods of darkening skin and/or hair. The present invention also relates to compositions that may be used for self-tanning or darkening skin or change and/or darken the color or shade of hair.

2. Description of the Prior Art

Despite the known detriments of ultraviolet exposure, such as erythema, sunburn and incident sun damage, consumers still desire to increase the pigmentation of their skin, i.e. "tanning", that occurs when the skin is exposed to ultraviolet radiation. The cosmetic industry has attempted to fill the needs of consumers by providing tanning products that do not require ultraviolet exposure. These products are known as self-tanning products.

Typically, such self-tanning products contain dihydroxyacetone ("DHA"). DHA imparts a brown color by binding to proteins on the outer layer of skin. Since the outer layer of skin continually sloughs off, the results are temporary. In addition, tans obtained by DHA often appear unnaturally orange or yellow, as well as uneven or "streaky". Consumers of self-tanning products would prefer a product that imparts a more natural looking, more aesthetically pleasing tan.

Also, a natural tan, that occurs as a result of exposure to ultraviolet radiation, results in an increase in darkening of the skin. This increase in pigmentation also protects the skin against subsequent exposure to ultraviolet exposure.

Sunless tanning products that rely on dying agents, such as DHA, do not affect the amount or quality of pigments in the skin. Thus, such products do not provide protection against subsequent ultraviolet exposure. Clearly, consumers of self-tanning agents desire a product that will provide the added benefit of protection from the effects of subsequent exposure to ultraviolet radiation.

The prior art discusses increasing pigmentation of skin by the use of melanotropic peptides. However, melanotropic peptides present unwanted side effects.

There are also consumers who desire products that change and/or darken the color or shade of hair.

Thus, there is a desire for a composition that can provide tanning of skin without exposure to the sun. There is also a desire for a composition that when topically applied provides photoprotection from subsequent exposure to ultraviolet radiation, especially from the sun. Further, there is a desire for such a composition that will also change and/or darken the color or shade of hair.

SUMMARY OF THE INVENTION

It is an object of the present invention to provide a composition that increases melanin production in the skin and/or hair.

It is another object of the present invention to provide a composition that increases the pigmentation of skin and/or hair.

It is still another object of the present invention to provide a composition having methylthioadenosine in an amount effective to increase the pigmentation of skin and/or hair.

It is a further object of the present invention to provide a method of increasing melanin production in the skin and/or hair without exposure to the sun.

These and other objects and advantages of the present invention are achieved by a composition having methylthioadenosine. Preferably, the methylthioadenosine is present in an effective amount about 0.001 wt % to about 20 wt % of the total weight of the composition.

The present invention also provides a method of increasing melanin production in skin and/or hair. The method includes applying to the skin and/or hair, an effective amount of methylthioadenosine, in a cosmetically and/or pharmaceutically acceptable vehicle.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
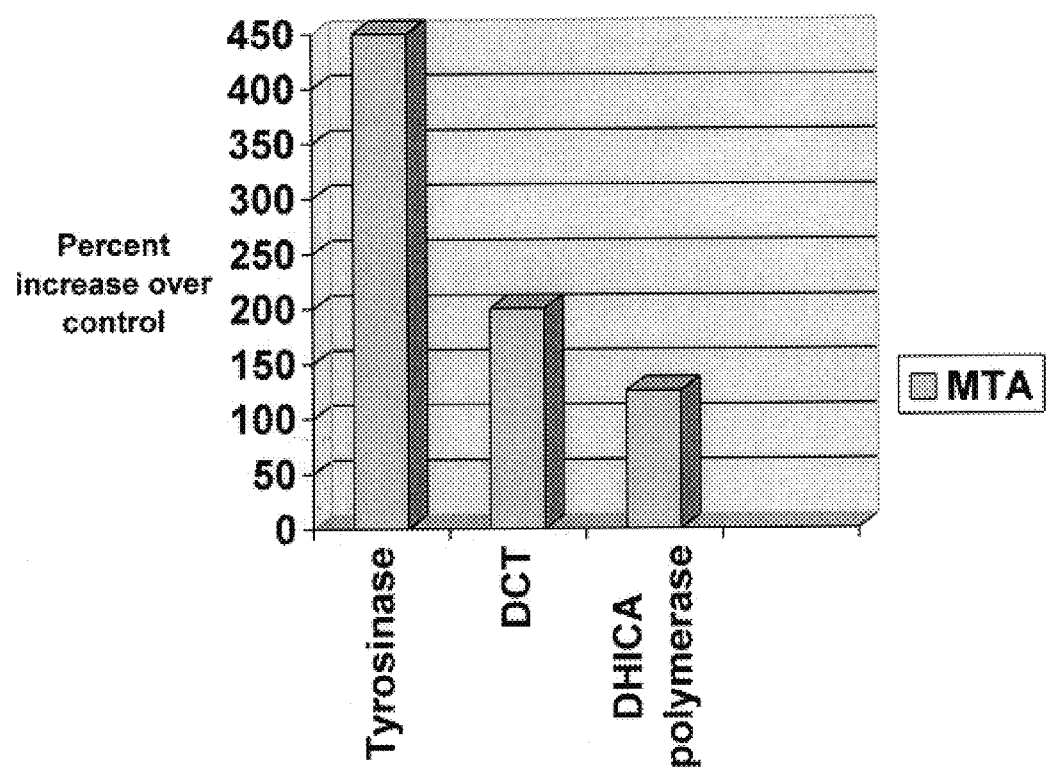
FIG. 1 shows the percent increase of melanin (relative to a control) demonstrated in the tyrosinase assay, dopachrome tautomerase assay and DHICA polymerase assay described in Example 1 below.

The present invention relates to methods for self-tanning or darkening skin and/or darkening the color or shade of hair. The present invention also relates to compositions that provide self-tanning or darkening of skin and/or darkening of the color or shade of hair.

The present invention relates to the use of 5'-deoxy-5'-methylthioadenosine ("MTA" or "methylthioadenosine") for tanning or darkening skin, as well as for increasing pigmentation, and thus darkening the color or shade, of hair. The present invention also relates to a topical composition having MTA for increasing pigmentation of skin and/or hair.

Methylthioadenosine is generally defined by the following formula:

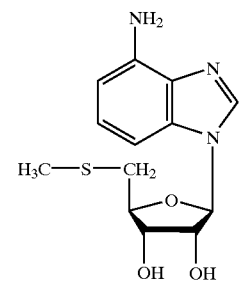

The present invention stimulates an increase in pigmentation of skin by modifying the melanin synthesis pathway set forth below.

Melanin Synthesis Pathway

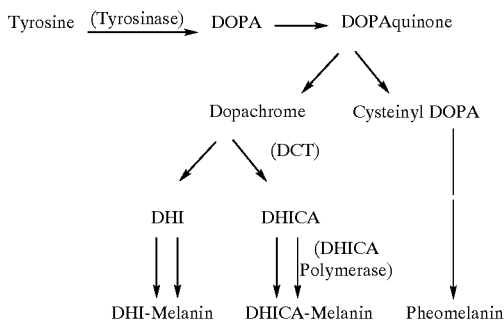

Referring to this melanin synthesis pathway, the conversion of tyrosine to melanin involves several steps. The present invention improves/alters pigmentation by altering, i.e. increasing, the activity of certain enzymes in the melanin synthesis pathway. In particular, it has been found that MTA increases (1) the conversion of tyrosine to dihydroxyphenylalanine ("DOPA") by accelerating tyrosinase, (2) the conversion of DOPAchrome to 5,6-dihydroxyindole-2-carboxylic acid ("DHICA") by accelerating DOPAchrome tautomerase ("DCT"), and (3) the polymerization of DHICA to DHICA-melanin by accelerating DHICA polymerase. By modifying and/or altering the activity of these enzymes, the present invention provides increased pigmentation, even without exposure to ultraviolet radiation, and/or increased photoprotection by increasing melanin levels.

In addition, there are three distinct types of melanin present in the skin, namely DHI-melanin, DHICA-melanin and pheomelanin. While it is difficult to clearly calculate or quantify absolute proportions of DHI, DHICA, mixed and pheomelanin in the skin, altering the enzymatic activity, and thus the relative proportions of these three types of melanin in the skin, also provides a novel way to alter, namely darken, skin color.

Also, an increase in tyrosinase activity coupled with an increase in dopachrome tautomerase (DCT) and DHICA polymerase activity, enriches the formation of DHICA-melanin. DHICA-melanin has photoprotective activity. Thus, the application of MTA not only enriches the pigmentation in the epidermis, even absent exposure to ultraviolet radiation, but it provides the skin with protection against subsequent exposure to the sun and/or ultraviolet radiation.

Thus, this discovery also provides compositions that are useful for increasing melanin production. These compositions have MTA, preferably in a topical carrier.

Although it is possible according to the present invention to administer MTA alone, it is preferable to administer it as part of a topical composition. Such a composition has MTA, in an amount effective to provide the benefits set forth in this application, in a pharmaceutically or a cosmetically acceptable vehicle.

Examples of such pharmaceutically or cosmetically acceptable vehicles include, but are not limited to, water; glycerin; alcohols such as ethanol, propyl alcohol and fatty alcohol; oils such as vegetable, mineral and silicone; fatty ether; fatty ester; glycol; polyglycol; or any combinations thereof. The composition may be in the form, among other forms, of a solution, water-in-oil emulsion or oil-in-water emulsion.

Preferably, the topical compositions of the present invention will have MTA in the amount about 0.001 percentage by weight or weight percent (wt %) to about 20 wt % based on the total weight of the composition. The MTA in such compositions is present preferably in an amount about 0.02 wt % to about 10 wt % and more preferably in an amount about 0.05 wt % to about 5 wt %, based on the total weight of the composition.

Additional ingredients may be incorporated into compositions of the present invention to provide suitable cosmetically and/or pharmaceutical compositions. Examples of such additional ingredients include, but are not limited to, one or more emulsifiers (e.g., anionic, cationic or nonionic), botanical extracts, chelating agents, colorants, emollients, film formers, fragrances, humectants, lubricants, moisturizers, preservatives, skin penetration enhancers, stabilizers, rheology modifiers, or any combinations thereof.

The topical compositions of the present invention may also include other active agents. Such other active agents may include, but are not limited to, one or more anti-aging agents (e.g., anti-wrinkling agents), anti-allergenic agents, antifungals, antiseptics, exfollients, insect repellents, sunscreens, vitamins, or any combinations thereof.

Compositions may be formulated in any convenient form suitable for topical application to the skin. Such forms include an aerosol spray, gel, cream, dispersion, emulsion, foam, liquid, lotion, mousse, pomade, powder, pump spray, solid, solution, stick or incorporated into a patch or towelette. The compositions may be incorporated in a design or pattern on a material for transfer to the skin to provide a temporary tattoo or mendhi-type design on the skin.

To increase pigmentation of the skin as part of a self-tanning regimen, it is preferred that MTA or a composition having MTA is applied to the skin at least once daily for at least three days, preferably five days to one week.

In self-tanning preparations, the compositions may also include dihydroxyacetone ("DHA"). The DHA may be present in an amount up to about 20 wt % of the total weight of the composition. Preferably, DHA will be present in an amount about 0.01 wt % to about 10 wt %, and more preferably about 0.5 wt % to about 3 wt %, based on the total weight of the composition. The combination of DHA and MTA in a self-tanning product is particularly useful to give the skin immediate color by the DHA. As the quantity of melanin increases, it is believed that the natural tone provided by MTA will provide a superior aesthetically pleasing tan as compared to DHA-only self-tanning products presently on the market.

The method of application of the aforementioned compositions will typically depend on the formulation or composition used. For example, self-tanning compositions will be applied to the skin either by applying a solution, cream or gel having MTA to the skin, or by aerosol or other spray delivery of the composition to the desired area of the skin.

Similarly, compositions that are intended to increase the pigmentation in hair can be topically applied to that area of the hair in which increased pigmentation, i.e. darkening, is desired. In particular, to change and/or darken the color or shade of hair, the compositions having MTA should be rubbed onto/into the scalp so that the composition can penetrate into the hair follicles or root shafts and be absorbed into the hair during the melanin-production process.

EXAMPLES

The effect of MTA on the melanin synthesis pathway is demonstrated below with various assays using mouse melanoma cells from the S91 cell line.

Example 1

Tyrosinase Assay

A tyrosinase assay was done according to the method outlined in Chakraborty et al., 1989, Melanogenic regulatory factors in coated vesicles from melanoma cells, J. Invest. Dermatol. 93: 616–620. Specifically, mouse melanoma cells were dissolved with the addition of 0.1 M sodium phosphate buffer, pH 6.8, containing Triton X-100 (1% vol/vol), at a ratio of 1–5×10⁶ cells/ml. After 10 minutes on ice, the extracts were centrifuged at 4° C. (10,000 g, for 10 minutes) and the supernatant fractions were assayed for tyrosinase. Tyrosinase was assayed spectrophotometrically by adding up to 0.1 ml cell extract to 0.2 ml of a solution of freshly prepared DOPA (~0.5 mg/ml), in a total volume of 0.5 ml of 0.1 M sodium phosphate buffer, pH 6.8. Reactions were carried out at 37° C. in plastic cuvettes, and the appearance of absorption at 475 nm was followed.

Pellets of $10^6$ cells were solubilized by boiling in 1 M NaOH for 10 minutes. Insoluble cell debris was removed by centrifugation. Spectrophotometric analysis of melanin content was conducted at 400 nm. The melanin content per milligram protein was calculated and normalized against the vehicle control. As illustrated in FIG. 1, the tyrosinase assay demonstrated that MTA, even at a very low concentration of 0.02%wt/volume (vol.), increases tyrosinase activity about 400 to about 500 percent as compared to the vehicle control (DMSO), which is an about 4 to about 5 fold increase.

Example 2

DOPAchrome Tautaumerase Assay

DOPAchrome Tautaumerase (DCT) activity was assayed according to the method disclosed in Chakraborty et al., 1998, Effect of arbutin on melanogenic proteins in human melanocytes, Pigment Cell Res. 11: 206–212. Specifically, ice-cold DOPA (0.5 mg per ml of 0.1 M sodium phosphate buffer, pH 6.8) was mixed with Ag2O (30 mg Ag2O: 1 mg DOPA) for about 1 minute and filtered through a 0.22. μm Millipore filter. DCT was assayed spectrophotometrically by adding up to 0.1 ml cell extract to 0.5 ml of a solution of freshly prepared DOPAchrome (~0.5 mg/ml). Reactions were carried out at room temperature in plastic cuvettes, and the disappearance of absorption at 475 nm was followed. Phenylthiourea (1 mM) was added to the reaction mixture, because the presence of tyrosinase in the cell extract can interfere with the assay. The percentage conversion of DOPAchrome was calculated per mg of protein extract and normalized against the vehicle control. As illustrated in FIG. 1, MTA increases DCT activity about 200 to about 250 percent, as compared to the vehicle control (DMSO), which is an increase of about 2 to about 2.5 fold.

Example 3

DHICA Polymerase Assay

A DHICA polymerase assay was done according to the method disclosed in Chakraborty et al., 1996, Polymerization of 5,6-dihydroxyindole-2-Carboxylic acid to melanin by the pmel17/silver locus protein, Eur. J. Biochem. 236: 180–188. Specifically, the cell extract (0.5 ml, 150–200 μg protein) was passed through a wheat germ agglutinin column (1 ml bed volume) equilibrated with lysis buffer. The bound material was eluted with 0.5 ml 1M N-acetyl glucosamine, which contains crude DHICA polymerization factor and other melanogenic proteins. A reaction mixture of 0.5 ml containing either the enzyme preparation to be measured (20 μg protein from wheat germ agglutinin equates) or the appropriate buffer blank, DHICA (0.5 mM), and 100 mM sodium phosphate buffer, pH 7.0. Phenylthiourea was also included to inhibit endogenous tyrosinase activity in the preparation.

Spectrophotomeric reading of the absorbance of the reaction mixture was taken at T=0 and T=4h time points at 400 nm. DHICA-melanin, but not DHICA itself, has been shown to absorb light at these wavelengths (Orlow et al., 1992, Synthesis and characterization of melanins from dihydroxyindole-2-carboxylic acid and dihydroxyndole, Pigment Cell Res. 5: 113–121). An increase in absorbance over that seen in blank tubes was defined as specific DHICA polymerization factor activity. As illustrated in FIG. 1., MTA increased DHICA polymerase activity about 150 percent, which is an increase of about 1.5 fold.

Example 4

Visual Melanin Assay

Cells were cultured in 1:1 mixture of Ham F10+10% horse serum and DMEM+10% fetal bovine serum. All cell experiments were conducted in a humidified, 5% CO2 incubator at 370 C. The basal level of pigmentation of these cells is determined to identify the effect of pigmentogenic compounds visually from the color of the cell pellet. The basal level is illustrated in FIG. 4. Cells were treated with 0.02%wt/vol. and 0.05%wt/vol. concentrations of MTA respectively, based on the total weight of the composition), for 12, 24, 48, and 72 hours to provide a visual melanin assay. The visual melanin assay of 0.02%wt/vol. MTA versus the dimethylsulfoxide ("DMSO") vehicle control at 12, 24, 48 and 72 hours is photographically depicted in FIG. 2. The visual melanin assay of 0.05%wt/vol. MTA versus the dimethylsulfoxide ("DMSO") vehicle control at 12, 24, 48 and 72 hours is photographically depicted in FIG. 3. FIG. 4 illustrates the pigment level in untreated cells at 0 hours.

Figure 2:
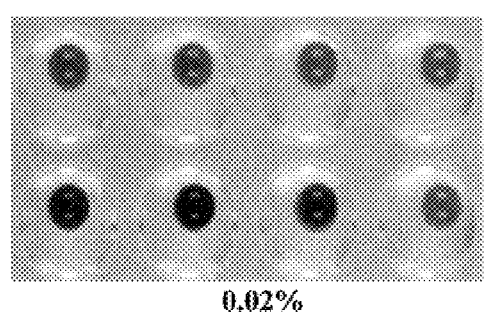
FIG. 2 is a color photograph comparing pigment levels in mouse melanoma cells treated with 0.02%wt/vol. methylthioadenosine versus a vehicle control.
Figure 3:
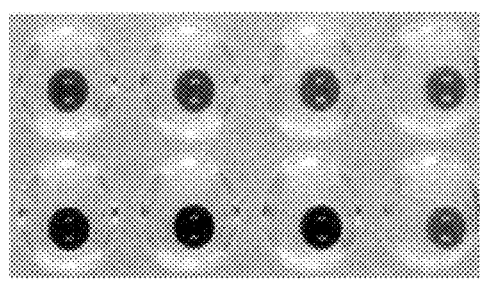
FIG. 3 is a color photograph comparing pigment levels in mouse melanoma cells treated with 0.05%wt/vol. methylthioadenosine versus a vehicle control.
Figure 4:
FIG. 4 is a color photograph illustrating the pigment level in untreated mouse melanoma cells at 0 hours.

The results shown in FIGS. 2 to 4 demonstrate a marked increase in the pigment levels of the cells treated with both concentrations of MTA (0.02%wt/vol. and 0.05%wt/vol.), as compared to the cells treated with DMSO and to those left wholly untreated. In particular, there is a particularly marked difference in pigmentation levels after 24 hours.

The following is an example of a self-tanning lotion to having MTA.

| INGREDIENT | WT % |
| --- | --- |
| MTA | 0.001 TO 20 |
| Butylene glycol | 2 |
| Methyl paraben | 0.2 |
| Propyl paraben | 0.1 |
| Imidazolidinyl urea | 0.3 |
| Ceteareth-6/stearyl alcohol (e.g., CREMOPHOR A 6 (BASF)) | 3 |
| Ceteareth-25 (e.g., CREMOPHOR A 25 (BASF)) | 1.5 |
| Glyceryl stearate (CREMOPHOR GS 11 (BASF)) | 3 |
| Cetyl Alcohol | 3 |
| Cetearyl octanoate (e.g., LUVITOL EHO (BASF)) | 6 |
| Benzyl laurate (e.g., LUVITOL BL (BASF)) | 6 |
| Dimethicone, 50 cst | 0.5 |
| Water | QS to 100 |

It should be understood that the foregoing description and examples are only illustrative of the present invention, and are not offered as limitations. Various alternatives and modifications can be devised by those skilled in the art without departing from the present invention. Accordingly, the present invention is intended to embrace all such alternatives, modifications and variations that fall within the scope of the appended claims.

What is claimed is:

1. A composition comprising methylthioadenosine in an amount effective to increase pigmentation and a cosmetically acceptable vehicle suitable for application to skin, scalp or hair.

2. The composition of claim 1, wherein the methylthioadenosine is present in an amount about 0.001 wt % to about 20 wt % based on the total weight of the composition.

3. The composition of claim 1, wherein the methylthioadenosine is present in an amount about 0.02 wt % to about 10 wt % based on the total weight of the composition.

4. The composition of claim 1, wherein the methylthioadenosine is present in an amount about 0.05 wt % to about 5 wt % based on the total weight of the composition.

5. The composition of claim 1, wherein the composition provides self-tanning of skin.

6. The composition of claim 1, further comprising dihydroxyacetone.

7. The composition of claim 6, wherein the dihydroxyacetone is present in an amount about 0.5 wt % to about 3 wt % based on the total weight of the composition.

8. The composition of claim 6, wherein the composition provides self-tanning of skin.

9. A method of darkening skin, scalp and/or hair comprising topically applying to skin, scalp and/or hair a dopachrome tautomerase accelerator in an amount effective to increase pigmentation.

10. The method of claim 9, wherein the dopachrome tautomerase accelerator is methylthioadenosine.

11. The method of claim 9, wherein the dopachrome tautomerase accelerator is in a cosmetic or pharmaceutical composition prior to being applied to the skin, scalp and/or hair.

12. The method of claim 11, wherein the skin is self-tanned when the composition is topically applied to the skin.

13. The method of claim 12, wherein the composition further comprises dihydroxyacetone.

14. A method of darkening skin, scalp and/or hair comprising topically applying to skin, scalp and/or hair an effective amount of a DHICA-polymerase accelerator.

15. The method of claim 14, wherein the DHICA-polymerase accelerator is methylthioadenosine.

16. The method of claim 14, wherein the DHICA-polymerase accelerator is in a cosmetic or pharmaceutical composition prior to being applied to the skin, scalp or hair.

17. The method of claim 16, wherein the skin is self-tanned when the composition is applied to the skin.

18. The method of claim 17, wherein the composition further comprises dihydroxyacetone.

19. A method of accelerating tyrosinase activity in skin, scalp and/or hair comprising topically applying to the skin, scalp and/or hair a composition having an effective amount of methylthioadenosine.

20. The method of claim 19, wherein the composition provides self-tanning of skin.

* * * * *